(12) United States Patent
Park et al.

(10) Patent No.: US 9,999,224 B2
(45) Date of Patent: Jun. 19, 2018

(54) ANTIMICROBIAL REVERSE THERMAL GEL AND METHODS OF FORMING AND USING SAME

(71) Applicants: Daewon Park, Englewood, CO (US); Maria Bortot, Denver, CO (US); Vikas Patel, Denver, CO (US)

(72) Inventors: Daewon Park, Englewood, CO (US); Maria Bortot, Denver, CO (US); Vikas Patel, Denver, CO (US)

(73) Assignee: The Regents of the University of Colorado, a body corporate, Boulder, CO (US)

( * ) Notice: Subject to any disclaimer, the term of this patent is extended or adjusted under 35 U.S.C. 154(b) by 0 days. days.

(21) Appl. No.: 15/110,703

(22) PCT Filed: Jan. 9, 2015

(86) PCT No.: PCT/US2015/010888
§ 371 (c)(1),
(2) Date: Jul. 8, 2016

(87) PCT Pub. No.: WO2015/106149
PCT Pub. Date: Jul. 16, 2015

(65) Prior Publication Data
US 2016/0366890 A1    Dec. 22, 2016

Related U.S. Application Data

(60) Provisional application No. 61/926,163, filed on Jan. 10, 2014.

(51) Int. Cl.
*A01N 47/34* (2006.01)
*C08G 81/02* (2006.01)

(52) U.S. Cl.
CPC ........... *A01N 47/34* (2013.01); *C08G 81/024* (2013.01)

(58) Field of Classification Search
CPC ............................. A01N 47/34; C08G 81/024
See application file for complete search history.

(56) References Cited

U.S. PATENT DOCUMENTS 5,632,727 A    5/1997   Tipton
2012/0244369 A1    9/2012   Ober

FOREIGN PATENT DOCUMENTS

| WO | WO2011/109732 | * | 9/2011 |
| WO | 2013166198 A1 | | 11/2013 |
| WO | 2014179615 A2 | | 11/2014 |

OTHER PUBLICATIONS

Li et al. (Angew. Chem. Int. Ed. 2013, 52,674-678).*
Park et al. (Biomaterials, Jan. 2011: 32(3) 777-786).*
International Search Report dated Jun. 2, 2015 in corresponding International Publication No. WO2015106149.

* cited by examiner

*Primary Examiner* — Anna Falkowitz
(74) *Attorney, Agent, or Firm* — Snell & Wilmer L.L.P.

(57) ABSTRACT

Antimicrobial polymers, composition including the polymers, and methods of forming and using the polymers and compositions are disclosed. The compositions have reverse thermal gelling properties and transform from a liquid to a gel—e.g., near or below body temperature, such as a skin temperature in an operating room. The polymers and compositions can be applied to a surface, such as a surface of skin proximate an incision site prior to surgery, to provide a relatively sterile area near the site.

18 Claims, 12 Drawing Sheets

ANTIMICROBIAL REVERSE THERMAL GEL AND METHODS OF FORMING AND USING SAME

CROSS-REFERENCE TO RELATED APPLICATIONS

This application is the national stage entry of International Application No. PCT/US15/010888, entitled ANTIMICROBIAL REVERSE THERMAL GEL AND METHODS OF FORMING AND USING SAME, filed on Jan. 9, 2015, and claims the benefit of U.S. Provisional Application Ser. No. 61/926,163, filed Jan. 10, 2014, entitled ANTIMICROBIAL REVERSE THERMAL GEL AND METHODS OF FORMING AND USING SAME, the contents of which are hereby incorporated herein by reference.

FIELD OF DISCLOSURE

The present disclosure generally relates to antimicrobial polymers, to compositions including the polymers, and to methods of forming and using the compositions and polymers. More particularly, the invention relates to antimicrobial compositions having reverse thermal gel properties, to polymers including antimicrobial functional groups, to methods of forming the polymers and compositions, and to methods of using the compositions.

BACKGROUND OF THE DISCLOSURE

Surgical site infections (SSIs), which are defined as infections that develop in the body during a surgical procedure or up to 30 days thereafter, are a significant source of nosocomial infections and lead to a significant number of prolonged illnesses and deaths each year. It is estimated that SSIs account for about 25-38% of nosocomial infections among surgical patients, which equates to about 2 million infections in the United States annually. Due, at least in part, that many kinds of pathogens such as MRSA, Gram positive/negative rods, and Gram-positive cocci are easily found in hospital air samples, the risk of SSIs is expected to increase. As a result, post-operative stays and associated costs are expected to increase.

Numerous protocols list preventive measures to reduce the risk of SSIs, such as surgical team hand/forearm antisepsis, antimicrobial prophylaxis, operation room management, asepsis of surgical tools, and postoperative incision care. In addition, some skin preparation products containing iodophor, alcohol, or chlorhexidine gluconate have been developed to assist with the disinfection process. Although most of these products act as a broad spectrum of topical antiseptics, skin bacteria continues to survive after treatment.

Figure 1:
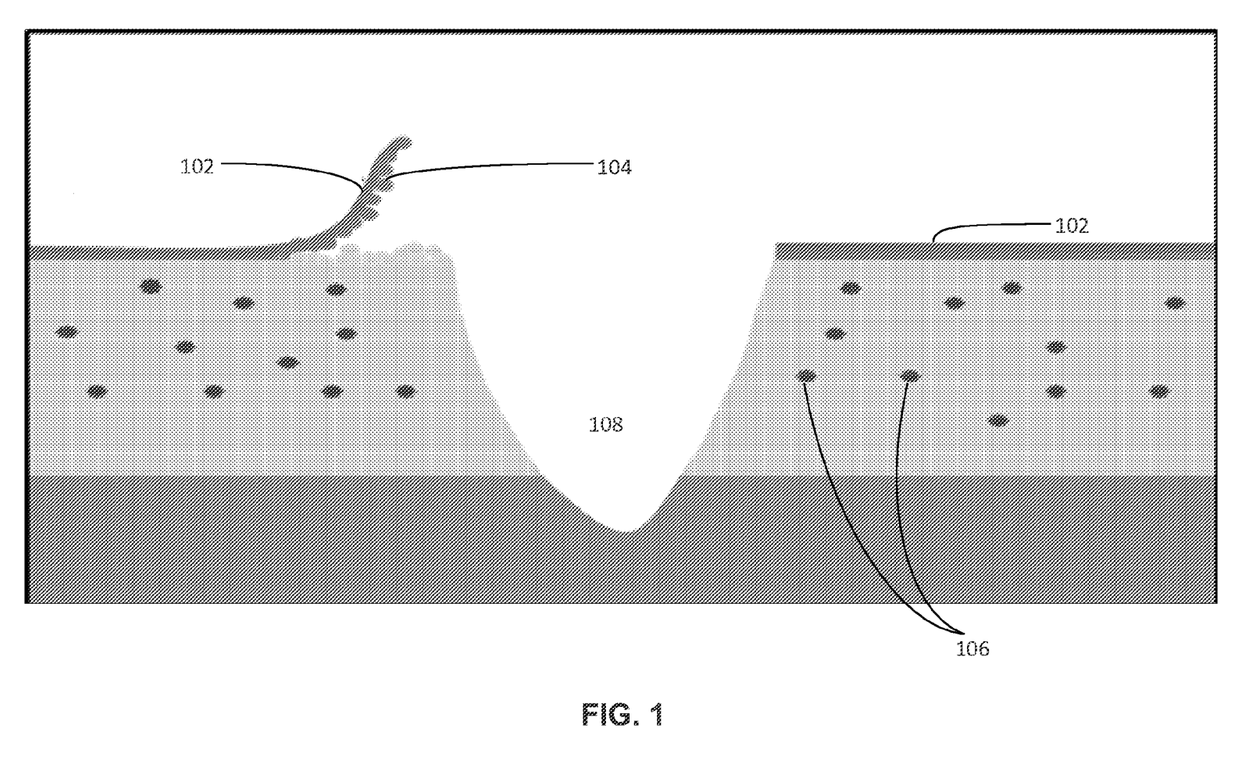
FIG. 1 illustrates epidermal cell detachment during removal of surgical incision drape.

Plastic surgical incision drapes, which are antiseptic-impregnated drapes, are used as an additional preventive measure against the spread of SSIs. The surgical drapes are most widely used to immobilize and sequester the skin flora and thus mitigate endogenous contamination of the surgical site from microbes residing on or within the patient's own skin. Surgical drapes have been used as common practice during surgeries for approximately 50 years. However, most of the currently available surgical incision drapes have numerous disadvantages. For example, surgical drapes generally provide only temporary protection against bacterial infections and some patients show an allergic reaction to active component (e.g., iodine) of some drapes. Further, in terms of clinical application, medical professionals often complain that the placement process of the drapes is time consuming and that the drapes often do not remain well-attached to the skin surface, leading to an increase in infection risk. In addition, when drapes 102 are removed, for example near and incision 108, a layer of epidermal cells 104 can be detached, exposing flora 106 found beneath the top surface of skin, thereby increasing risk of secondary bacterial infection, as illustrated in FIG. 1.

Figure 5:
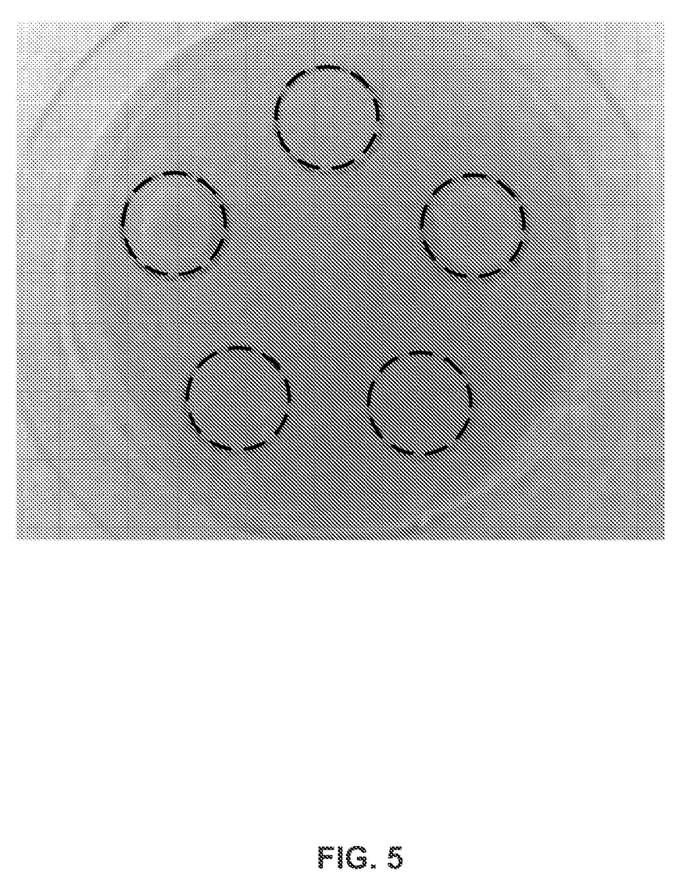
FIG. 5 illustrates bacterial growth after inoculation with used surgical incision drapes.

FIG. 5 illustrates bacterial growth after inoculation with used surgical incision drapes. For the test, pieces of surgical incision drapes were taken right after a surgery, and inoculated on 5 spots of LB agar plate, and cultured for 48 hr. Surprisingly, a formation of bacterial colony was observed on 2 spots, indicating the bacterial recolonization.

Furthermore, current surgical incision drapes are designed for single use, resulting in undesired expense and waste. And, a size of a surgical drape can depend on the size of the patient and/or surgical incision, requiring size selection of the surgical drape which adds to prep time and inventory requirements.

Accordingly, improved systems, compositions, and methods for mitigating the onset and/or spread of infections, such as SSIs, and which reduce cost, waste, and/or inventory requirements are desired.

SUMMARY OF THE DISCLOSURE

The present disclosure generally relates to antimicrobial compositions with reverse thermal gel properties, to polymers having antimicrobial functional groups, to methods of forming the compositions and polymers, and to methods of using the compositions and polymers. As set forth in more detail below, the compositions and polymers described herein can be used as an antimicrobial coating on a surface, such as skin on a patient prior to surgery, to mitigate risk of infections, such as SSIs, to the patient. The compositions can be used to, for example, replace and/or supplement use of surgical drapes.

In accordance with exemplary embodiments of the disclosure, an antimicrobial reverse thermal gel composition is a liquid at below a temperature, such as a body temperature or slightly below and becomes a gel at or near (e.g., slightly below) a body or skin temperature (e.g., the composition forms a gel at a temperature of about 25° C. to about 50° C., or about 28° C. to about 50° C., or about 30° C. to about 48° C.). Because the composition is a liquid below a body or skin temperature, the composition can be sprayed onto a desired area (e.g., skin proximate an incision site). As the composition warms—e.g., to a skin temperature, the composition transitions to a gel.

In accordance with further exemplary embodiments of the disclosure, an antimicrobial composition includes a polymer having an antimicrobial functional group (e.g., a quaternized amine group), wherein the antimicrobial reverse thermal gel composition is liquid at a temperature of about 15° C., 20° C., 25° C., 28° C., or 30° C. or less and the antimicrobial reverse thermal gel material transitions to a gel at a temperature of about 25° C., 28° C., or 30° C. or more (or at about a temperature of skin in an operating room). In accordance with various aspects of these embodiments, the polymer comprises or is a copolymer comprising a reverse thermal gel block (e.g., a PSHU-PNIPAAm block) and an antimicrobial functional group block (e.g., comprising a quaternized amine group). Alternatively, as set forth below, the polymer can include a branched polymer with one or more antimicrobial groups and reverse thermal gel properties. In accordance with exemplary aspects of these embodiments, the polymer includes a polyurea-polyurethane polymer backbone. By way of examples, the polymer comprises the general formula:

PNIPAAm-NH-PSHU

Q-PSHU where, for example, x ranges from about 17-350, y ranges from about 18-61, n ranges from about 15 to about 900, and/or m ranges from about 6-22. In accordance with further aspects, the antimicrobial reverse thermal gel composition comprises, consists essentially of, or consists of the polymer and a carrier—e.g., comprising a diluent—e.g., water or ethanol. The composition can include, for example, about 2 wt % to about 20 wt %, about 5 wt % to about 15 wt %, or about 8 wt % to about 10 wt % polymer in solution comprising, consisting of, of consisting essentially of the polymer and the carrier.

In accordance with further exemplary embodiments of the invention, an antimicrobial reverse thermal gel composition includes a copolymer comprising an antimicrobial functional group block and a reverse thermal gel block or portion. The composition can comprise, consist essentially of, or consist of the copolymer and a carrier, which can consist of, consist essentially of, or comprise a diluent—e.g., water or ethanol. The functional groups, the formula, and/or the polymer backbone can be the same or similar to those described above. The composition can include, for example, about 2 wt % to about 20 wt %, about 5 wt % to about 15 wt %, or about 8 wt % to about 10 wt % polymer in solution.

In accordance with yet further exemplary embodiments of the disclosure, a method of forming an antimicrobial polymer includes the steps of: synthesizing PSHU from urea N-BOC-serinol and a diisocyanate, conjugating PNIPAAm-COOH onto the PSHU, and quaternatizing an —NH$_2$ group (e.g., by exposing the —NH$_2$ group to hexyl bromide).

In accordance with additional embodiments of the disclosure, an antimicrobial reverse thermal gel composition comprises a branched polymer comprising one or more antimicrobial groups or sections and a reverse thermal gel section. In accordance with various aspects of these embodiments, the antimicrobial section comprises one or more quaternized amine groups. In accordance with further aspects, the reverse thermal gel section comprises or is derived from branched polyethylenimine (PEI), such as the branched PEI shown below.

Exemplary PEI

An exemplary branched polymer can have a general formula of:

where n ranges from about 2 to about 60, and y ranges from about 15 to about 900. Although illustrated with particular quaternized amine groups, other amine groups can additionally or alternatively be quaternized. A conjugation of the branched polymer can range from about 30% to about 60% or about 20% to about 30%. Exemplary compositions in accordance with these embodiments can have the same reverse thermal gel and other properties described above. Further, the compositions can comprise, consist essentially of, or consist of the branched polymer and a carrier, which can consist of, consist essentially of, or comprise a diluent— e.g., water or ethanol. The compositions can include, for example, about 2 wt % to about 20 wt %, about 5 wt % to about 15 wt %, or about 8 wt % to about 10 wt % polymer in solution (e.g., comprising diluent).

In accordance with further embodiments, an exemplary method of forming a branched reverse thermal gel composition comprises the steps of conjugating PNIPAAm-COOH onto the PEI, and quaternatizing an —NH2 group (e.g., by exposing the —NH2 group to hexyl bromide).

In accordance with yet additional exemplary embodiments of the disclosure, a method of using an antimicrobial compound includes the steps of providing an antimicrobial reverse thermal gel, such as a composition as described herein, and applying (e.g., spraying) the antimicrobial reverse thermal gel composition to a surface—e.g., skin of an animal, such as a human. The composition can be applied to a patient prior to surgery to mitigate the risk of infection, such as an SSI, to the patient. In accordance with various aspects of these embodiments, the composition can be easily removed from the surface by applying a solution (e.g., comprising a diluent) having a temperature below the gel transition temperature of the composition.

In accordance with yet further exemplary embodiments of the disclosure, a polymer comprises a general formula of:

FIGS. 3 (A) and (B) illustrate gelling properties of a composition in accordance with exemplary embodiments of the disclosure.

It will be appreciated that the figures are not necessarily drawn to scale. For example, the dimensions of some of the elements in the figures may be exaggerated relative to other elements to help to improve understanding of illustrated embodiments of the present invention.

PNIPAAm-NH-PSHU                                    Q-PSHU where, for example, x ranges from about 17 to about 350, y ranges from about 18 to about 61, n ranges from about 15 to about 900, and/or m ranges from about 6 to about 22.

As noted above, the compositions and polymers described herein can be used in lieu of surgical drapes, and thus can reduce costs and waste associated with surgical procedures.

BRIEF DESCRIPTION OF THE DRAWING FIGURES

A more complete understanding of exemplary embodiments of the present disclosure may be derived by referring to the detailed description and claims when considered in connection with the following illustrative figures.

DETAILED DESCRIPTION OF EMBODIMENTS OF THE DISCLOSURE

The description of exemplary embodiments of the present disclosure provided below is merely exemplary and is intended for purposes of illustration only; the following description is not intended to limit the scope of the invention disclosed herein. Moreover, recitation of multiple embodiments having stated features is not intended to exclude other embodiments having additional features or other embodiments incorporating different combinations of the stated features.

Various exemplary embodiments of the disclosure provide a reverse thermal gel composition that includes a polymer and optionally a carrier. The composition can be used to prevent or mitigate risk of infection, such as SSIs. Exemplary compositions exhibit better adhesion to skin or other surfaces compared to surgical drapes, thus reducing or eliminating potential infections—e.g., infections cause by removal of a surgical drape. Further, use of the compositions can reduce waste (e.g., by replacing surgical drapes) and costs associated with surgical procedures and with SSIs that might otherwise occur. In addition, use of exemplary compositions, as described herein, can reduce a surgical prep time and surgical inventory requirements. Further, exemplary compositions are non-leaching—in contrast to some antibacterial materials that are used with typical surgical drapes.

In accordance with further exemplary embodiments of the disclosure, the composition is a water-soluble material (or soluble in another diluent, such as ethanol) below the composition's gel transition temperature and maintains a solution state at low temperature whilst turning into a physical gel upon heating (e.g. upon contact with human skin). This property allows the composition to be easily sprayed on the patient's skin and form a layer of antimicrobial gel on the skin surface. During use, (e.g., during surgery) the gel might dry out and form a film on the skin; however, the film can maintain its antimicrobial activity even if dried. Moreover, since the composition returns to solution state at low temperature, the composition can be easily removed by washing with cold water (or cold alcohol) without the risk of epidermal cell layer detachment.

In accordance with various aspects of exemplary embodiments, the composition can transition from a gel to a liquid state at a low temperature environment (e.g., 15° C., 20° C., 25° C., 28° C., or 30° C. or less). Exemplary compositions are designed to remain in place after application until removed with a cold solution. For example, the composition can remain in place for a period of about 1 to about 12 hours.

Exemplary antimicrobial reverse thermal gel compositions include a polymer having an antimicrobial functional group, wherein the antimicrobial reverse thermal gel composition is liquid at a temperature below a skin temperature in an operating room or, e.g., 15° C., 20° C., 25° C., 28° C., or 30° C. or less and the antimicrobial reverse thermal gel material transitions to a gel at a temperature just below the skin temperature or about 25° C., 28° C., or 30° C. or more. In accordance with additional or alternative embodiments, an antimicrobial reverse thermal gel composition includes a copolymer comprising an antimicrobial functional group block and a reverse thermal gel block. Alternatively, the polymer can include, for example, a branched polymer.

An exemplary polymer includes a polyuria-polyurethane polymer backbone that is functionalized with a reverse thermal gel group and an antimicrobial group. The reverse thermal gel block can include, for example, a PNIPAAm functional group to facilitate formation of a reverse thermal gel. The antimicrobial functional group block can include, for example, one or more quaternized amine groups. In accordance with other exemplary embodiments, the polymer includes a branched polymer having a reverse thermal gel group (e.g., having a PNIPAAm functional group) and an antimicrobial group (e.g., one or more quaternized amine groups).

The polymers including the quaternized amine groups can kill bacteria and other microbes on contact. The bactericidal action mechanism of the quaternized amine compounds (polymers) is thought to occur through interactions between positively charged polymer sites and the negatively charged bacteria cell wall. The cationic sites of the quaternary ammonium compounds are adsorbed onto anionic sites of the cell-wall by electrostatic interaction, followed by a significant lipophilic component promoting diffusion through the cell wall. Acting as a surfactant, the long hydrophobic alkyl chains are able to disrupt the cytoplasmic membrane and cause the release of electrolytes and nucleic materials leading to cell death. As set forth in more detail below, exemplary compositions are effective at killing various microbials, including *Staphylococcus aureus* subsp. *aureus* Mu3 (MRSA/hetero-VISA), *Staphylococcus epidermidis*, *E. coli.*, and the like.

Figure 2:
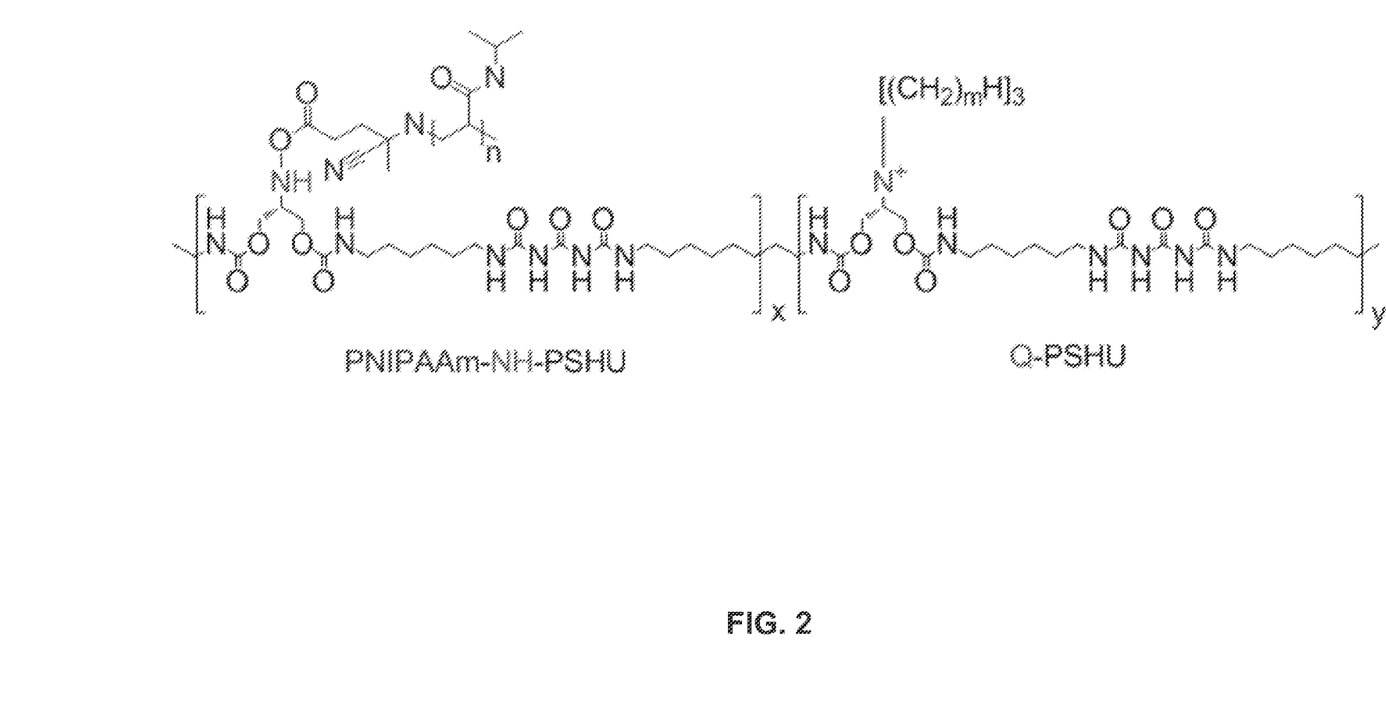
FIG. 2 illustrates an exemplary polymer formulation in accordance with various embodiments of the disclosure.

An exemplary polymer formulation is illustrated in FIG. 2, where, for example, x ranges from about 17-350, or about 17 to about 330, or about 17 to about 310; y ranges from about 18-61, or about 18 to about 51, or about 20 to about 41; n ranges from about 15 to about 900, or about 15 to about 800, or about 15 to about 400 and/or m ranges from about 6-22, or about 6 to about 20, or about 6-18. A percent of PNIPAAm conjugation can range, for example, from about 5 percent to about 55 percent, or about 10 to about 50 percent, or about 10 to about 45 percent.

Exemplary molecular weights of the polymer blocks and the overall copolymer are presented below.

Exemplary range of repeating unites of PNIPAAm (A) 17-310

Molecular weight of NIPAAM (B): 113.16 g/mol.

Exemplary range of molecular weight of PNIPAAM block: 2,000-35,000 g/mol.

Exemplary range of repeating units of PSHU (C): 20-41.

Molecular weight of PSHU (D): PSHU de-protected (no BOC groups): 489.57 g/mol.

Exemplary range of molecular weight of PSHU block prior to quaternization: 10,000-20,000 g/mol (by GPC: Mn=9,725 g/mol, Mw=12,512 g/mol).

After quaternization with three alkyl chains attached to PSHU.

Alkyl Chain length: 6-18.

Alkyl Chain molecular weight (E): 86.18-254.5 g/mol.

| Molecular weight of *PNiPAAM* component → i | Molecular weight of *PSHU* component → ii | Molecular weight of Alkyl chains component → iii |
|---|---|---|

Figure 6:
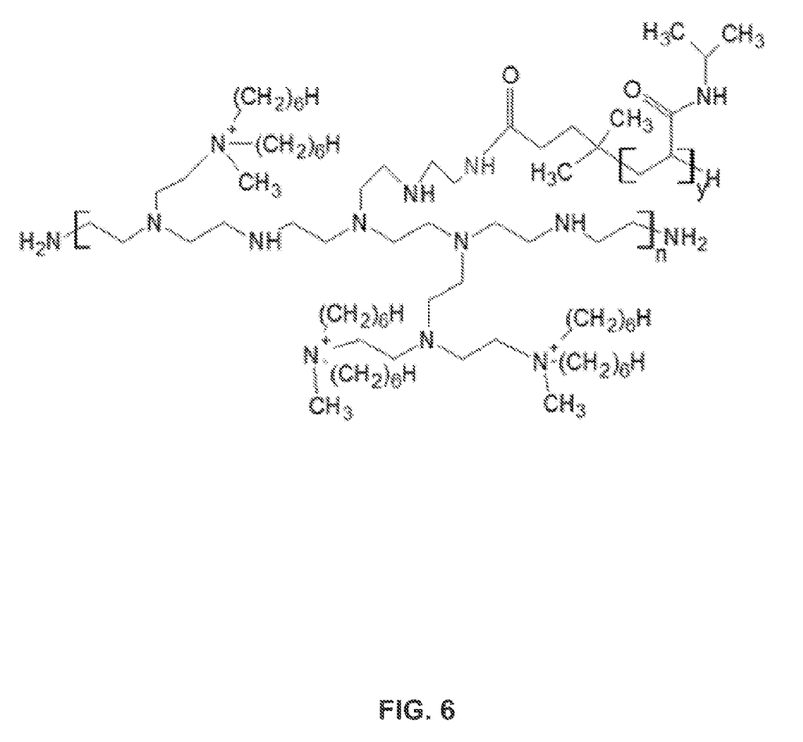
FIG. 6 illustrated another exemplary polymer formulation in accordance with various embodiments of the disclosure.
Figure 7:
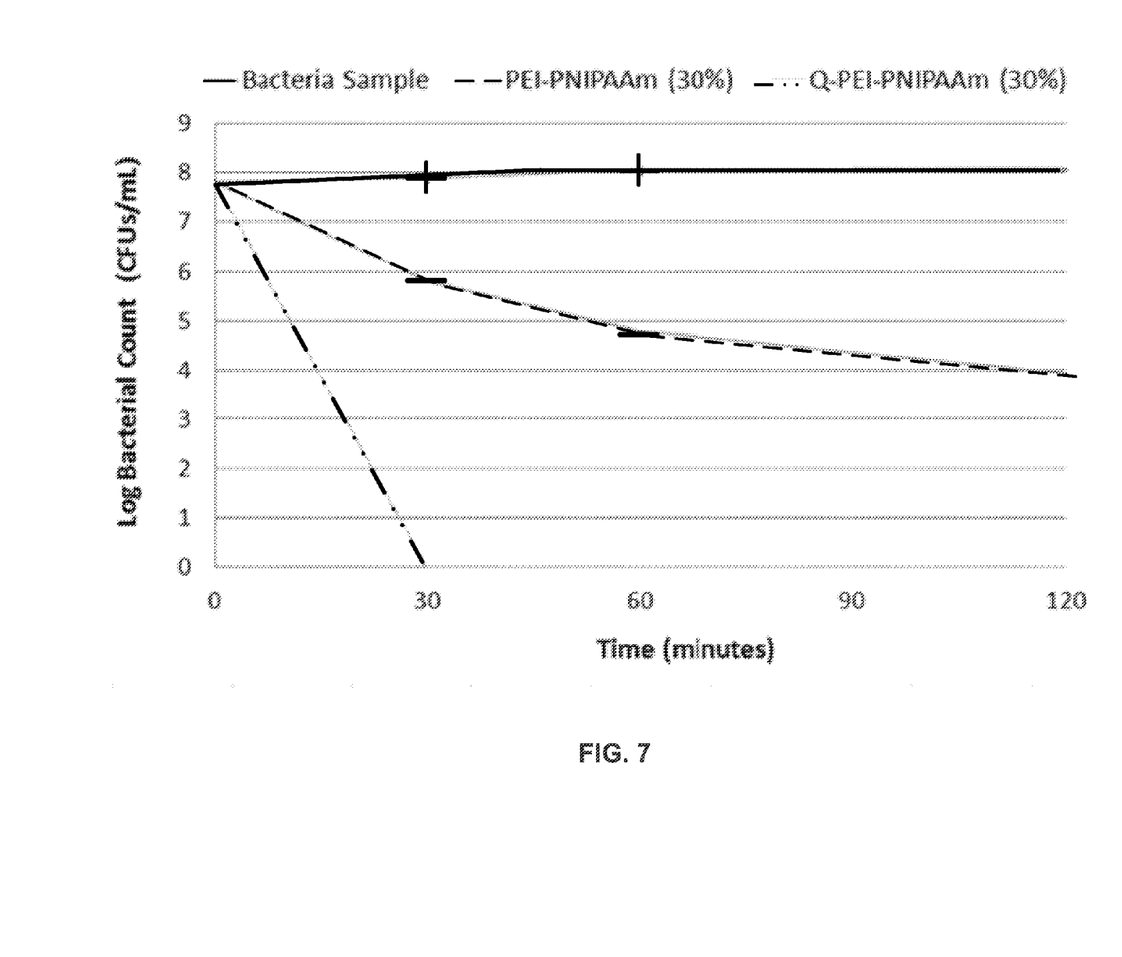
FIG. 7 illustrates effects of exemplary compositions on cultures of *Staphylococcus aureus* subsp. *aureus* Mu3 (MRSA/hetero-VISA) in accordance with various embodiments of the disclosure.

Total MW of $QuatPSHUPNIPAAM = [n \times C \times A \times B]_i + [C \times D]_{ii} + [3 \times E \times ((1-n) \times C)]_{iii}$ FIG. 6 illustrates another exemplary polymer composition. In accordance with exemplary aspects of the exemplary polymer illustrated in FIG. 6, n ranges from about 2 to about 60, and/or y ranges from about 15 to about 900. Although illustrated with particular quaternized amine groups, other amine groups can additionally or alternatively be quaternized. A conjugation of the branched polymer can range from about 30% to about 60% or about 20% to about 30%.

As the antimicrobial reverse thermal gel composition transitions from a liquid to a gel, the viscosity of the composition changes. For example, the viscosity of the composition before transition to a gel can ranges from less than 50 cp, less than 20 cp, or less than 10 cp at a temperature of 15° C., 20° C., 25° C., 28° C., or 30° C. or less or below a skin temperature prior to or during surgery. Additionally or alternatively, the composition can have a relatively high viscosity of greater than 50 cp, greater than 100 cp, or greater than 200 cp at a temperature of about 25° C., 28° C., or 30° C. or more, or at or slightly below a skin temperature prior to or during surgery.

An amount of time for the composition to gel and to return to liquid can vary in accordance with various factors, including a percent of polymer in the composition. Table 1 below illustrates gelation times for PSHU-PNIPAAm with about 15% PNIPAAm conjugation at a temperature of about 20° C. at various polymer concentrations in a carrier comprising water.

| Weight % of polymer in solution | Time to Gel (s) | Time to De-Gel (s) |
|---|---|---|
| 10% | 9.4 | 21.9 |
| 9% | 6.2 | 11.3 |
| 8% | 4.5 | 15.7 |
| 7% | 8.1 | 15.7 |
| 6% | 12.6 | 11.6 |
| 5% | 18.4 | Insrant |

Figure 3:
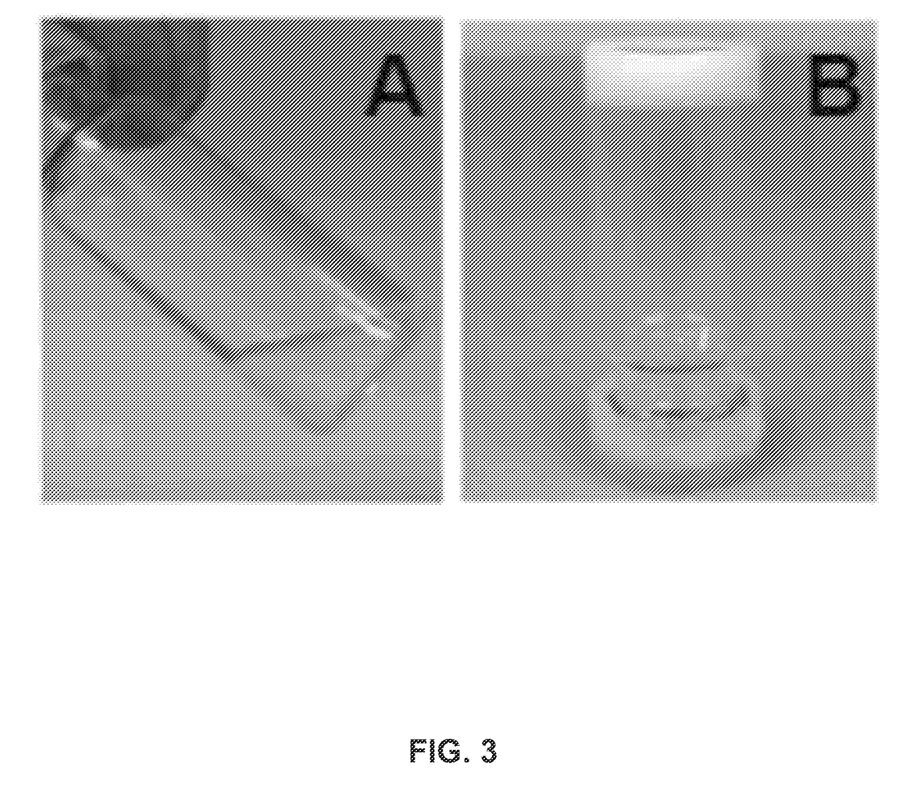

FIG. 3(A) illustrates thermal gelling properties of an exemplary aqueous composition at a low temperature, and (B) illustrates the composition after a transition to a gel at 37° C. In the illustrated case, the composition maintained its gel status over a broad range of temperature from 32° C.-45° C.

Compositions in accordance with exemplary embodiments can include the polymer dispersed in a carrier. In these cases, the carrier can include a diluent, such as water or alcohol. By way of examples, the compositions can comprise, consist of, or consist essentially of about 2 to about 20, about 5 to about 15, or about 8 to about 10 weight percent polymer in a carrier, and the carrier can comprise, consist of, or consists essentially the diluent. Exemplary diluents include water and ethanol.

Exemplary polymers can be formed using the following steps: 1) synthesis of PSHU using urea, N-BOC-serinol and a diisocyanate (e.g., hexamethylene diisocyanate), 2) conjugation of PNIPAAm-COOH onto PSHU, which results in PSHU-NIPAAm (in this step, the BOC protecting group in PSHU is de-protected to primary amines ($-NH_2$), and 3) quaternization of $-NH_2$ (e.g., using hexyl bromide (Br$(CH_2)_6H$)). Exemplary compositions can be formed by forming the polymer as described herein and mixing the polymer with a suitable carrier.

Exemplary diisocyanates suitable for use in synthesizing quaternized polyurethanes in accordance with the present invention include, but are not limited to isophorone diisocyanate, 1,4-phenylene diisocyanate, 1,3-phenylene diisocyanate, toluene-2,4-diisocyanate, toluene-2,6-diisocyanate, 2,4,6-trimethyl-1,3-phenylene diisocyanate, tetramethylene diisocyanate, octamethylene diisocyanate, 1,3-bis(1-isocyanato-1-methylethyl) benzene, 4,4'-methylenebis(phenyl isocyanate), 3,3'-dimethyloxy-4,4'-bisphenylene diisocyanate, 1,8 diisocyanateoctane, α,α,α',α'-tetramethyl-1,3-xylylene diisocyanate, and 3,3'-dimethoxy-4,4'-biphenylene diisocyanate.

In accordance with additional exemplary embodiments of the disclosure, exemplary polymers are formed by 1) conjugation of PNIPAAm-COOH onto PEI, which results in PEI-NIPAAm 2) quaternization of $-NH_2$ (e.g., using hexyl bromide (Br(CH2)6H)). Exemplary compositions can be formed by forming the polymer as described herein and mixing the polymer with a suitable carrier.

Antibacterial Tests

Figure 4:
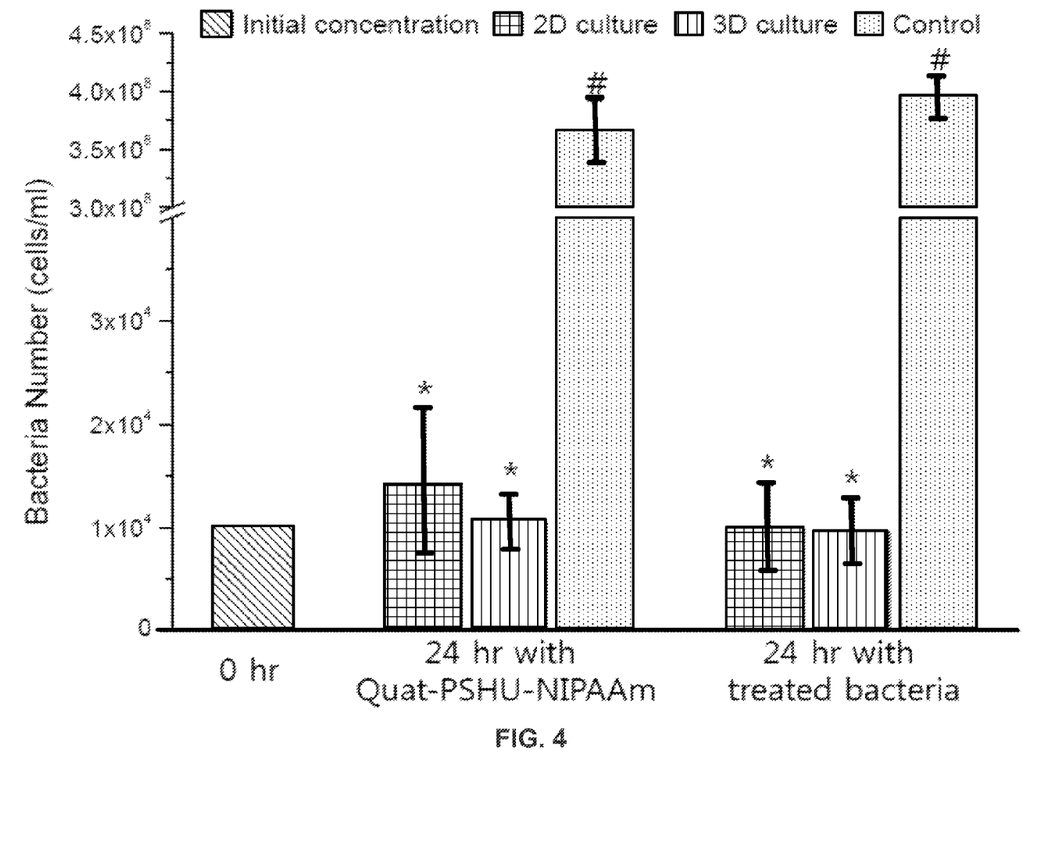
FIG. 4 illustrates antibacterial activity of an exemplary composition in accordance with exemplary embodiments of the disclosure.

FIG. 4 illustrates antibacterial activity of compositions formed in accordance with exemplary embodiments of the present disclosure—e.g., the polymer composition illustrated in FIG. 2. In the illustrated example, bacteria ($10^4$ S. aureus) were cultured under 2D and 3D conditions for 24 hr and the bacteria numbers were calculated using optical density data. For 2D culture, 10% (wt/v) polymer solution in 200 µl LB was added to a 24-well plate; this solution was then placed on a 37° C. hot plate to form a gel and 500 µl of the cell suspension was added. After 24 hr, the bacteria number was counted using optical density data. For 3D culture, cells were mixed with 10% (wt/v) polymer solution in 200 µl LB; this solution was then placed on a 37° C. hot plate to form a gel and 500 µl of LB was added. After 24 hr, the bacteria number was counted. No increase in cell number was found in both groups, while significant increase was observed in just LB. * ($p>0.1$) and # ($p<0.001$) represent statistical difference with 0 hr sample. To confirm that the polymer killed the cells after 24 hr-culture, $10^4$ cells were recovered from each group (named treated bacteria) and mixed with 500 µl of LB in 24-well plate. After 24 hr, the bacteria number was counted. No increase was observed with cells taken from polymer culture groups, indicating that all cells were killed by the polymer. However, the culture with the cells recovered from the LB increased as much as the first culture, indicating that no cells were killed.

FIG. 7-11 illustrate bactericidal properties of a composition including a polymer as illustrated in FIG. 6. In the example illustrated in FIG. 7, the polymer included about 30% PNIPAAm conjugation and the polymer was dissolved in about 10% w/v in $dh_2O$. The antimicrobial tests conducted using Q-PEI-PNIPAAm against stationary-phase cultures of S. aureus (Staphylococcus aureus subsp. aureus Mu3 (MRSA/hetero-VISA)) showed excellent results, over an 8-$log_{10}$ CFU/ml bacterial reduction. This test was conducted two more times to ensure the killing capacity of the polymer. The tests were carried out using different polymer samples and different bacteria cultures. Standard deviations were calculated, accounting for every sample. At the same time, it is also worth mentioning that PEI-PNIPAAm (30% conjugation, non quaternized) itself possesses antibacterial activity. This is due to the presence of protonated ammonium groups and non-protonated amine groups. The ethylene backbone serves as hydrophobic groups, which create repeating cationic, amphiphilic structures along the polymer backbone at a neutral pH without any further chemical modification. At the same time, it can be observed that the exemplary Q-PEI-PNIPAAm polymer exhibited a 2-, 3-, and 4-log reduction after 30, 60, and 120 minutes, which is significantly better that the PEI-PNIPAAm composition.

Figure 8:
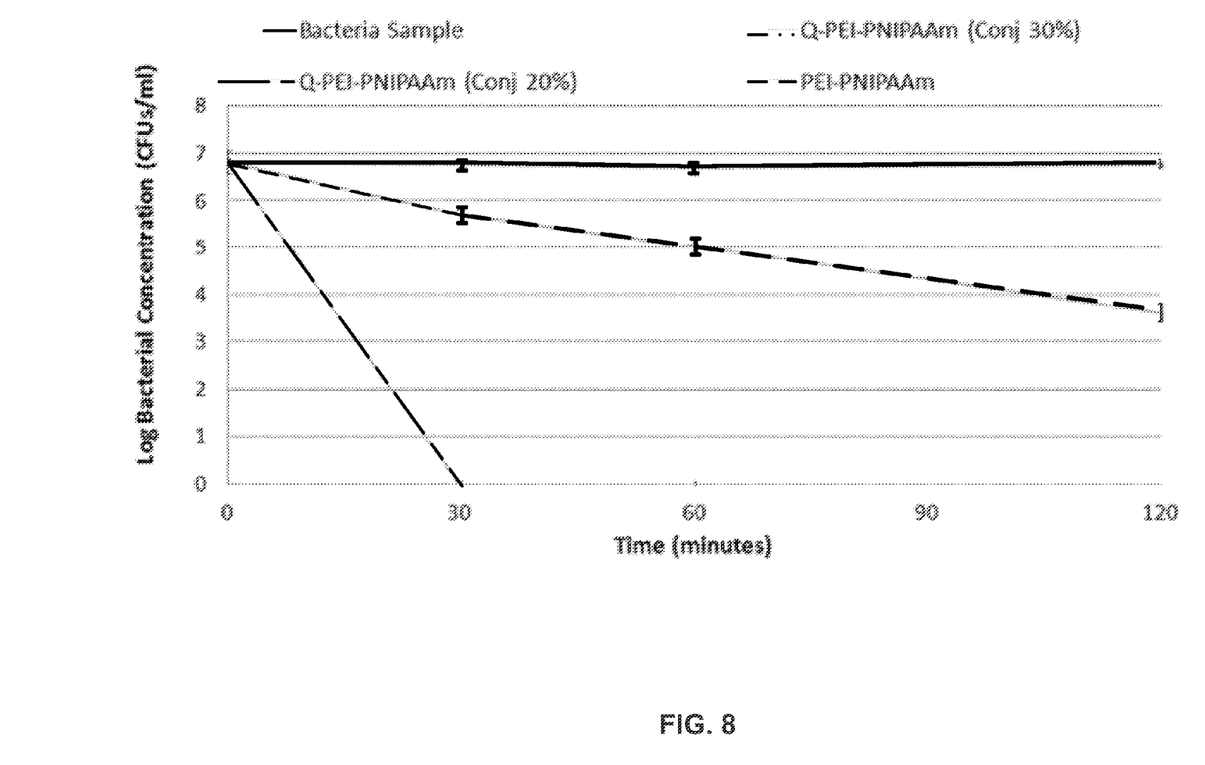
FIG. 8 illustrates effects of exemplary compositions on cultures of *Staphylococcus epidermidis* in accordance with various embodiments of the disclosure.

FIG. 8 illustrates bactericidal properties of the composition of FIG. 6 with 20% and 30% PNIPAAm conjugation and the polymer dissolved 10% w/v in $dh_2O$, evidencing that Q-PEI-PNIPAAm (20% and 30% conjugation) also exhibited an 8-$log_{10}$ bacterial reduction against Staphylococcus epidermidis. Q-PEI-PNIPAAm (20% and 30% conjugation) and PEI-PNIPAAm were added to stationary-phase cultures of Staphylococcus epidermidis. Samples were taken after 30, 60, and 120 minutes. Numbers indicate reductions in $log_{10}$ CFU/ml.

Figure 9:
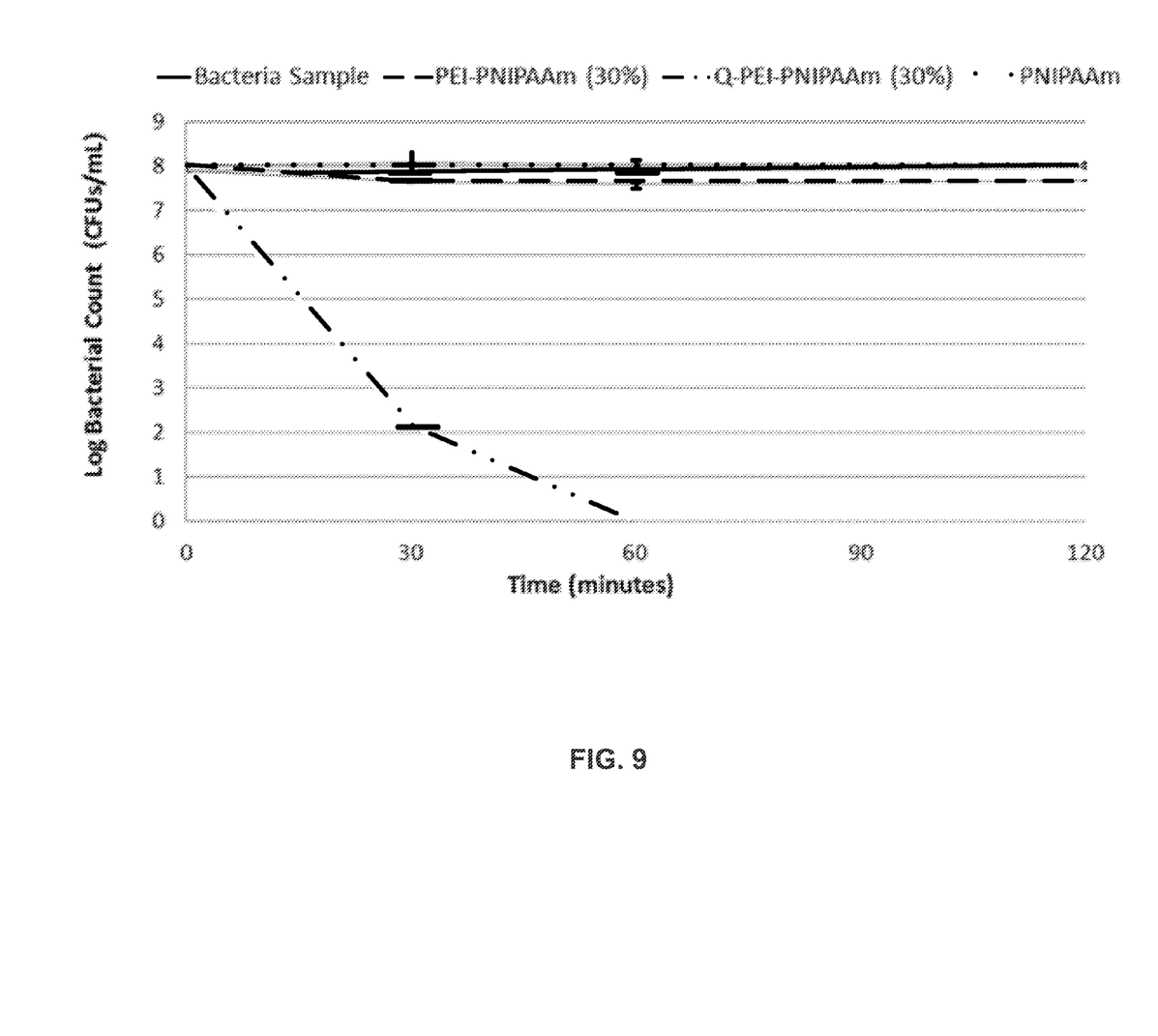
FIG. 9 illustrates effects of exemplary compositions on cultures of *Staphylococcus aureus* subsp. *aureus* Mu3 (MRSA/hetero-VISA) in accordance with additional embodiments of the disclosure.

FIG. 9 illustrates bactericidal properties of the composition of FIG. 6 with of 30% PNIPAAm conjugation dissolved 10% w/v in dh20 against S. aureus subsp. aureus Mu3 (MRSA/hetero-VISA). Q-PEI-PNIPAAm and PEI-PNIPAAm (30% conjugation) were added to stationary-phase cultures of Staphylococcus aureus subsp. aureus Mu3 (MRSA/hetero-VISA). Samples were taken after 30, 60, and 120 minutes. Numbers indicate reductions in $log_{10}$ CFU/ml. Once again, the test was conducted three times using different polymer samples and different bacteria cultures. Standard deviations were calculated, accounting for every sample. In this case, PEI-PNIPAAm (30% conjugation) also exhibited an 8-log 10 bacterial reduction, but the Q-PEI-PNIPAAm significantly outperformed the PEI-PNIPAAm. Two tests showed a 6-log 10 reduction in 30 minutes, while the third test showed an 8-log reduction was achieved in the same period of time. This variability is normal, and it was concluded that in 1 hour, the polymer was able to achieve an 8-log 10 bacteria reduction in all cases.

Figure 10:
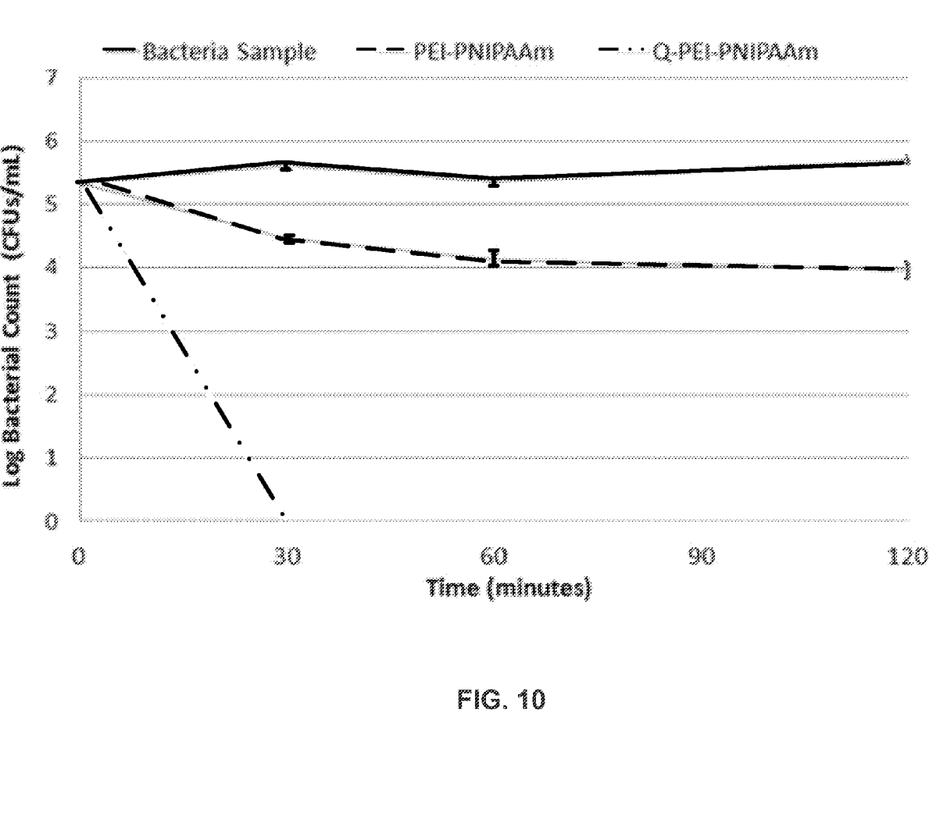
FIG. 10 illustrates effects of exemplary compositions on cultures of *Staphylococcus aureus* in accordance with further embodiments of the disclosure.

FIG. 10 illustrates results from Q-PEI-PNIPAAm and PEI-PNIPAAm (both 30% conjugation) dissolved in 10% w/v dh20 against *Staphylococcus aureus*. The polymer compositions were added to log-phase cultures of *Staphylococcus aureus*. Samples were taken after 30, 60, and 120 minutes. Numbers indicate reductions in log 10 CFU/ml. Some antibiotics require the cells to be multiplying in order to kill the bacteria. The mechanism of action of this polymer does not require this. But it may be important to ensure that the polymer can still be effective when subjected to continuously dividing cells. As can be observed in FIG. 10, Q-PEI-PNIPAAm (30% conjugation) achieved a 6-log bacteria reduction in 30 minutes.

Figure 11:
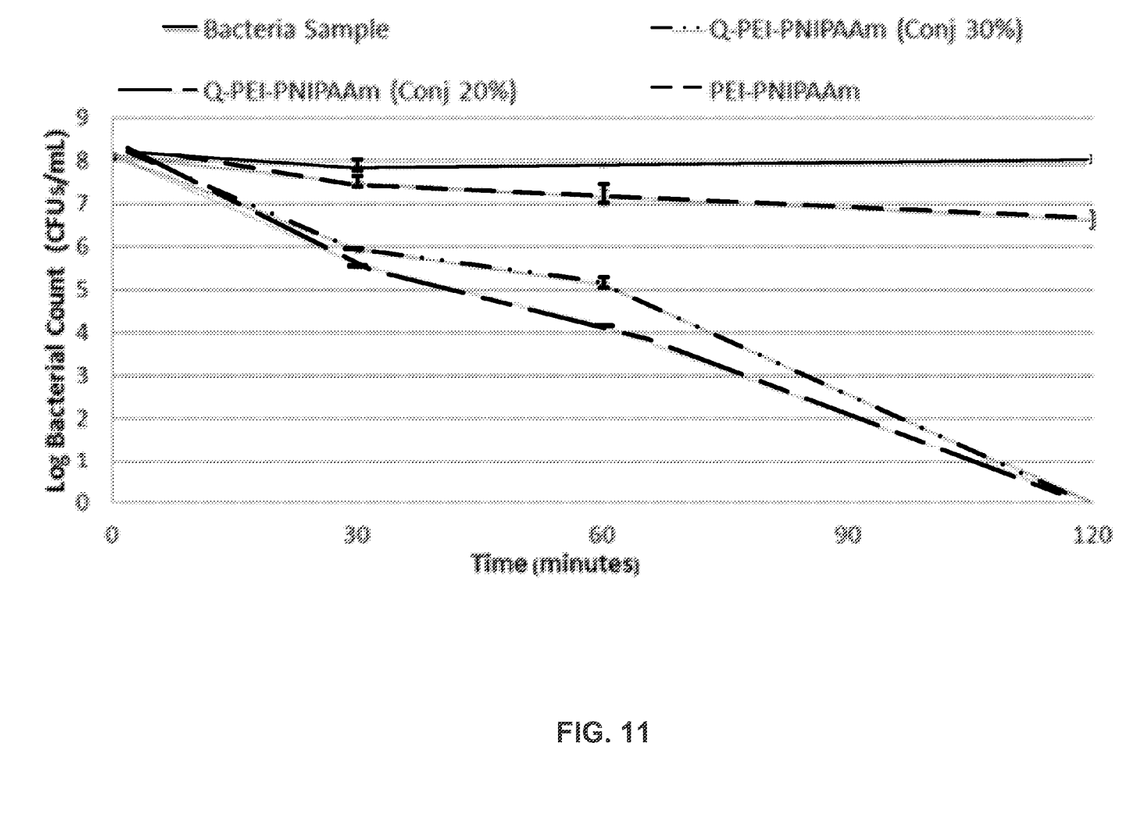
FIG. 11 illustrates effects of exemplary compositions on stationary-phase cultures of *E. coli.* in accordance with further embodiments of the disclosure.

FIG. 11 illustrates antibacterial results from Q-PEI-PNIPAAm (30% and 20% conjugation) and PEI-PNIPAAm (30% conjugation), each dissolved in 10% w/v dh20 against *Staphylococcus aureus*.

*Staphylococcus aureus* and *Escherichia coli* are among the most prevalent species of gram-positive and gram-negative bacteria. Antibacterial properties of Q-PEI-PNIPAAm (30% conjugation) were confirmed against gram-positive bacteria. Antibacterial properties of Q-PEI-PNIPAAm (30% conjugation) were then tested against gram-negative bacteria. Gram-positive bacteria generally have a thick cell wall, containing several layers of peptidoglycan, while gram-negative bacteria contains a similar cell wall, but is also surrounded by an outer membrane. This outer membrane can be harder to destabilize at times. Although gram-positive bacteria are prevalent on the skin, gram-negative bacteria can also be present in a clinical setting, and due to this, the polymer antibacterial activity against *E. coli* was assessed. Q-PEI-PNIPAAm (30% conjugation) exhibited a 2-, 3-, and 8-log 10 bacteria reduction after 30, 60, and 120 minutes, respectively. The lower bactericidal action, when compared to the previous tests, might be explained from the cell wall structural differences already mentioned between gram-positive and gram-negative bacteria. Q-PEI-PNIPAAm (20% conjugation) was also tested in this case, but only exhibited slightly higher bactericidal action. On the other hand, one of the controls, PEI-PNIPAAm (30% conjugation), had very little antibacterial activity, similar to the effect it had over the Mu3 strain of *S. aureus*.

Figure 12:
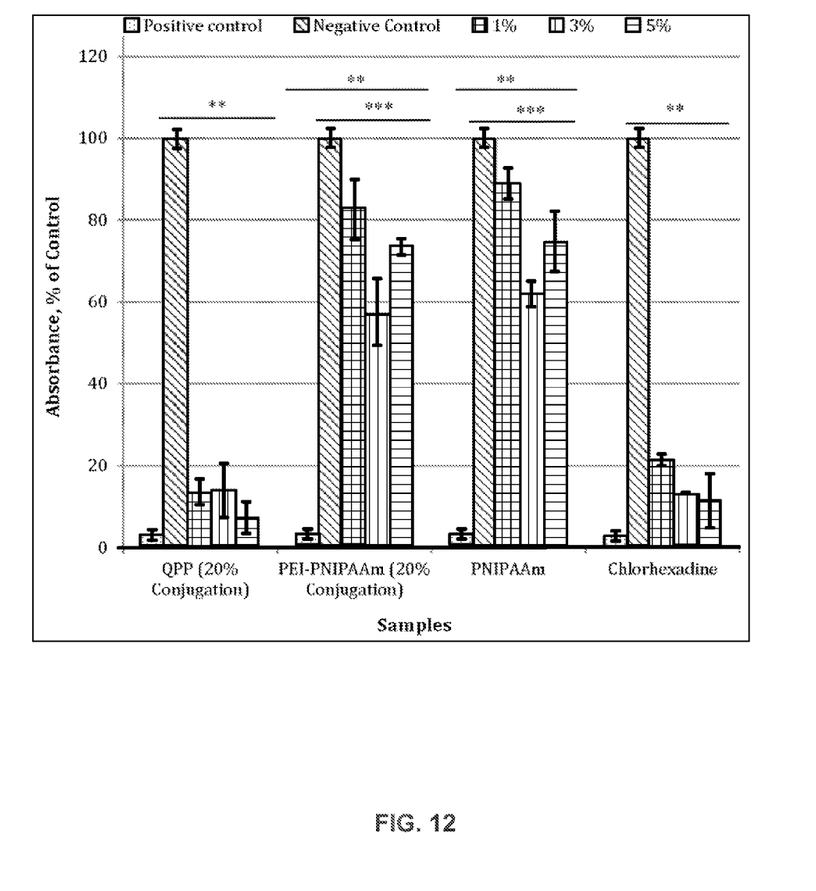
FIG. 12 illustrates absorbance percent of exemplary compositions in accordance with further embodiments of the disclosure.

FIG. 12 illustrates Cytotoxicity Tests of Q-PEI-PNIPAAm. An MTT assay was conducted to assess the biocompatibility of Q-PEI-PNIPAAm. Several methods were used to conduct this test. Previously, the Q-PEI-PNIPAAm polymer had been placed on top of the cells mixed with the media; however, due to the gelling nature of the sample the polymer was not in contact with the cells for long period of time. Due to this, the methodology was modified and the cells were plated on top of the polymer and then trypsinized and re-plated before conducting the test; however, trypsinizing, centrifuging and re-plating cells can lead to higher variability in number of cells per well and since the cells were not left to attached on the plates for long enough the results may be inaccurate. Finally the polymer was dissolved in alcohol, left to evaporate and then the cells were plated on top. Since the MTT measures absorbance, blanks were required for each sample. However, the layer of polymer on the plate needed to be very thin so the polymer concentration tested was 1, 3 and 5%. Q-PEI-PNIPAAm (20% Conjugation) was chosen for the tests, since it had a relatively high number of quaternized amine groups and was assumed to be relatedly more toxic. Chlorhexidine 2%, a common skin preparation solution was tested as a control.

FIG. 12 illustrates that no statistical difference was observed between negative control and cells exposed to PNIPAAm and PEI-PNIPAAm. A statistically significant difference was observed between the experimental samples, negative and positive control (cells cultured with 5% DMSO) (*indicates p>0.05, and indicates p<0.05.). No statistical difference between cells exposed to chlorhexidine (FDA approved) and Q-PEI-PNIPAAm was observed. The cells exposed to Q-PEI-PNIPAAm showed statistically significant difference in metabolic activity when compared to cells cultured with complete growth medium alone and to the ones exposed to 5% DMSO. Hence, a reduction in metabolic activity was observed but the same difference was obtained in the samples with cells subjected to an FDA approved skin preparation, chlorhexidine 2%.

An exemplary system in accordance with further embodiments of the disclosure includes a container (e.g., a spray bottle) and a composition as described herein. Exemplary use of the composition and/or system includes providing an antimicrobial reverse thermal gel composition as described herein and applying the composition to a surface—e.g., using a spray applicator or bottle. The composition can be applied to a surface, such as skin prior to a surgical procedure to reduce or mitigate SSIs.

The present invention has been described above with reference to a number of exemplary embodiments and examples. It should be appreciated that the particular embodiments shown and described herein are illustrative of the preferred embodiments of the invention and its best mode, and are not intended to limit the scope of the invention. It will be recognized that changes and modifications may be made to the embodiments described herein without departing from the scope of the present invention. These and other changes or modifications are intended to be included within the scope of the present invention.

We claim:

1. An antimicrobial reverse thermal gel composition comprising:

a polymer having an antimicrobial functional group, wherein the antimicrobial reverse thermal gel composition is liquid at a temperature of about 20° C. or less and the antimicrobial reverse thermal gel material transitions to a gel at a temperature of about 25° C. or more, and wherein the polymer comprises a polyurea-polyurethane polymer backbone.

2. The antimicrobial reverse thermal gel composition of claim 1, wherein the polymer comprises a copolymer comprising a reverse thermal gel block.

3. The antimicrobial reverse thermal gel composition of claim 1, wherein the polymer comprises an antimicrobial functional group block.

4. An antimicrobial reverse thermal gel composition comprising:

a polymer having an antimicrobial functional group, wherein the antimicrobial reverse thermal gel composition is liquid at a temperature of about 20° C. or less and the antimicrobial reverse thermal gel material transitions to a gel at a temperature of about 25° C. or more, wherein the polymer comprises a general formula of:

PNIPAAm-NH-PSHU                                   Q-PSHU

5. The antimicrobial reverse thermal gel composition of claim 4, where x ranges from about 17 to about 350.

6. The antimicrobial reverse thermal gel composition of claim 4, where y ranges from about 18 to about 61.

7. The antimicrobial reverse thermal gel composition of claim 4, where m ranges from about 6 to about 22.

8. The antimicrobial reverse thermal gel composition of claim 4, where n ranges from about 15 to about 900.

9. The antimicrobial reverse thermal gel composition of claim 4, wherein a percent of PNIPAAm conjugation ranges from about 10 percent to about 50 percent.

10. The antimicrobial reverse thermal gel composition of claim 4, wherein where x ranges from about 17 to about 330, y ranges from about 18 to about 61, and m ranges from about 6 to about 22.

11. The antimicrobial reverse thermal gel composition of claim 1 comprising a general formula of:

PNIPAAm-NH-PSHU                                   Q-PSHU where x ranges from about 17 to about 350;
y ranges from about 18 to about 61;
n ranges from about 15 to about 900; and
m ranges from about 6 to about 22.

12. The antimicrobial reverse thermal gel composition of claim 11, wherein a percent of PNIPAAm conjugation ranges from about 10 percent to about 50 percent.

13. The antimicrobial reverse thermal gel composition of claim 1, wherein the gelling time of the composition at a temperature of about 30° C. to about 45° C. ranges from about 5 to about 30 seconds.

14. A composition comprising the antimicrobial reverse thermal gel composition of claim 1.

15. The composition of claim 14, further comprising a diluent.

16. The composition of claim 15, wherein the diluent comprises water.

17. The composition of claim 15, wherein the diluent comprises alcohol.

18. The antimicrobial reverse thermal gel composition of claim 11,
where x ranges from about 17 to about 330;
y ranges from about 18 to about 51;
n ranges from about 15 to about 800; and
m ranges from about 6 to about 20.

* * * * *